US00PP15790P2

(12) United States Plant Patent
Jonkers

(10) Patent No.: US PP15,790 P2
(45) Date of Patent: Jun. 7, 2005

(54) **MINI *IMPATIENS* PLANT NAMED 'FIFY WHITE TWO'**

(50) Latin Name: *Impatiens walleriana*
Varietal Denomination: Fify White Two

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 31 days.

(21) Appl. No.: 10/818,377

(22) Filed: Apr. 5, 2004

(51) Int. Cl.[7] ..... A01H 5/00
(52) U.S. Cl. ..... Plt./317
(58) Field of Search ..... Plt./317

(56) References Cited

PUBLICATIONS

UPOV–ROM GTITM, Plant Variety Database, 2004/04, GTI Jouve Retrieval Software, Citation for *Impatiens* 'Fify White Two'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Mini *Impatiens* plant named 'Fify White Two', characterized by its compact, upright, outwardly spreading and mounded plant habit; freely branching habit; dense and bushy growth habit; dark green-colored leaves; freely flowering habit; and white-colored flowers that are positioned above and beyond the foliage.

1 Drawing Sheet

Botanical classification/cultivar designation: *Impatiens walleriana* cultivar Fify White Two.

BACKGROUND OF THE INVENTION

The present Invention relates to a new and distinct cultivar of Mini *Impatiens* plant, botanically known as *Impatiens walleriana,* and hereinafter referred to by the name 'Fify White Two'.

The new Mini *Impatiens* is a product of a planned breeding program conducted by the Inventor in Andijk, The Netherlands. The objective of the breeding program was to develop new compact Mini *Impatiens* cultivars with small flowers, freely branching and flowering habit, and attractive flower and foliage coloration.

The new *Impatiens* originated from a cross-pollination made by the Inventor in July, 2000, of a proprietary *Impatiens walleriana* selection identified as code number IW-778-1, not patented, as the female, or seed parent, with a proprietary *Impatiens walleriana* selection identified as code number MRO-1-52, not patented, as the male, or pollen parent. The cultivar Fify White Two was discovered and selected by the Inventor as a flowering plant within the progeny of the stated cross-pollination in a controlled environment in Andijk, The Netherlands in January, 2001.

Asexual reproduction of the new cultivar by terminal cuttings in Andijk, The Netherlands since January, 2001, has shown that the unique features of this new *Impatiens* are stable and reproduced true to type in successive generations of asexual reproduction.

SUMMARY OF THE INVENTION

The following traits have been repeatedly observed and are determined to be the unique characteristics of 'Fify White Two'. These characteristics in combination distinguish 'Fify White Two' as a new and distinct Mini *Impatiens* cultivar:

1. Compact, upright, outwardly spreading and mounded plant habit.
2. Freely branching habit; dense and bushy growth habit.
3. Dark green-colored leaves.
4. Freely flowering habit.
5. White-colored flowers that are positioned above and beyond the foliage.

Plants of the new *Impatiens* differ primarily from plants of the female parent selection in the following characteristics:

1. Plants of the new *Impatiens* are more vigorous than plants of the female parent selection.
2. Plants of the new *Impatiens* have larger flowers than plants of the female parent selection.

Plants of the new *Impatiens* differ primarily from plants of the male parent selection in the following characteristics:

1. Plants of the new *Impatiens* are smaller than plants of the male parent selection.
2. Plants of the new *Impatiens* have smaller flowers than plants of the male parent selection.

The new *Impatiens* can be compared to the *Impatiens walleriana* cultivar Firefly White, disclosed in U.S. Plant Pat. No. 11,407. However, in side-by-side comparisons conducted in Gilroy, Calif., plants of the new *Impatiens* differed from plants of the cultivar Firefly White in the following characteristics:

1. Plants of the new *Impatiens* had larger leaves than plants of the cultivar Firefly White.
2. Plants of the new *Impatiens* had larger flowers than plants of the cultivar Firefly White.
3. Plants of the new *Impatiens* had longer peduncles than plants of the cultivar Firefly White.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens*.

The photograph at the top of the sheet comprises a side perspective view of a flowering plant of 'Fify White Two'.

The photograph at the bottom of the sheet is close-up view of typical flowers and leaves of 'Fify White Two'.

DETAILED BOTANICAL DESCRIPTION

Plants of the cultivar Fify White Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Rooted young plants were planted in containers and had been growing for about five months when the photographs and the description were taken. In the following description, color references are made to The Royal Horticultural Society Colour Chart, 1995 Edition, except where general terms of ordinary dictionary significance are used.

Botanical classification: *Impatiens walleriana* cultivar Fify White Two.

Parentage:

*Female parent.*—Proprietary *Impatiens walleriana* selection identified as code number IW-778-1, not patented.

*Male parent.*—Proprietary *Impatiens walleriana* selection identified as code number MRO-1-52, not patented.

Propagation:

*Type cutting.*—Terminal cuttings.

*Time to initiate roots.*—About 10 to 21 days at 22 to 23° C.

*Time to produce a rooted young plant.*—About 28 days at 16 to 24° C.

*Root description.*—Fine, fleshy; white in color.

*Rooting habit.*—Freely branching.

Plant description:

*General appearance.*—Compact, upright, outwardly spreading and mounded plant habit.

*Growth and branching habit.*—Moderately vigorous and freely-branching growth habit with about 22 basal branches; lateral branches potentially forming at every node; dense and bushy growth habit. Pinching enhances branching.

*Plant height.*—About 13 cm.

*Plant diameter or spread.*—About 32 cm.

*Lateral branches.*—Length: About 15 cm. Diameter: About 4.5 mm. Internode length: About 8 mm. Texture: Smooth, glabrous. Color: 144A.

*Foliage description.*—Arrangement: Alternate, simple. Length: About 3.3 cm. Width: About 2.1 cm. Shape: Elliptical. Apex: Acute. Base: Attenuate. Margin: Slightly crenate with minute ciliation. Texture, upper and lower surfaces: Smooth, glabrous. Venation pattern: Pinnate. Color: Developing and fully expanded foliage, upper surface: 147A. Developing and fully expanded foliage, lower surface: 147B. Venation, upper and lower surfaces: 147B. Petiole: Length: About 1.3 cm. Diameter: About 2 mm. Texture, upper and lower surfaces: Smooth, glabrous. Color: 147D.

Flower description:

*Flower type and habit.*—Numerous small single flowers. Flowers arise from leaf axils. Freely flowering, usually about 38 flowers and flower buds per lateral branch. Flowers positioned above the foliage and typically face upright or outward. Flowers last about five to seven days on the plant under greenhouse conditions. Flowers persistent. Flowers not fragrant.

*Natural flowering season.*—Flowering is continuous through the spring and summer.

*Flower size.*—Height: About 2.5 cm. Diameter: About 2.3 cm. Depth: About 1 cm.

*Flower buds.*—Length: About 8 mm. Diameter: About 4 mm. Shape: Ovoid. Color: 155A.

*Petals.*—Quantity/arrangement: Five per flower in a single whorl. Length, banner petal: About 9 mm. Length, lateral petals: About 1 cm. Length, basal petals: About 1.2 cm. Width, banner petal: About 1.1 cm. Width, lateral petals: About 8 mm. Width, basal petals: About 8 mm. Shape: Obovate. Apex: Rounded or slightly emarginate. Base: Attenuate. Margin: Entire. Texture, upper and lower surfaces: Smooth, glabrous. Color: When opening, upper surface: 155A. When opening, lower surface: More white than 155D. Fully opened, upper surface: 155D. Fully opened, lower surface: More white than 155D.

*Sepals.*—Quantity/arrangement: Five in a single whorl; one modified into an elongated spur. Calyx length: About 4 mm. Calyx diameter: About 4 mm. Shape: Elliptic. Apex: Acute. Margin: Entire. Texture, upper and lower surfaces: Smooth, glabrous. Color, upper and lower surfaces: Close to 144A. Spur length: About 2.5 cm. Spur diameter: At flower, about 2 mm; at apex, less than 1 mm. Spur color: 145B.

*Peduncles.*—Length: About 1.4 cm. Diameter: About 1.5 mm. Angle: About 45° from vertical. Strength: Strong. Texture: Smooth, glabrous. Color: 144C.

*Reproductive organs.*—Stamens: Quantity: Five fused around stigma. Anther length: About 2 mm. Anther color: 8C. Pollen amount: Scarce. Pollen color: 8C. Pistils: Quantity per flower: One. Pistil length: About 3 mm. Stigma shape: Rounded. Stigma color: 157A. Style color: 147A. Ovary color: 147A.

*Seed/fruit.*—Seed and fruit production have not been observed.

Disease/pest resistance: Plants of the new *Impatiens* have not been observed to be resistant to pathogens and pests common to *Impatiens*.

It is claimed:

1. A new and distinct cultivar of Mini *Impatiens* plant named 'Fify White Two', as illustrated and described.

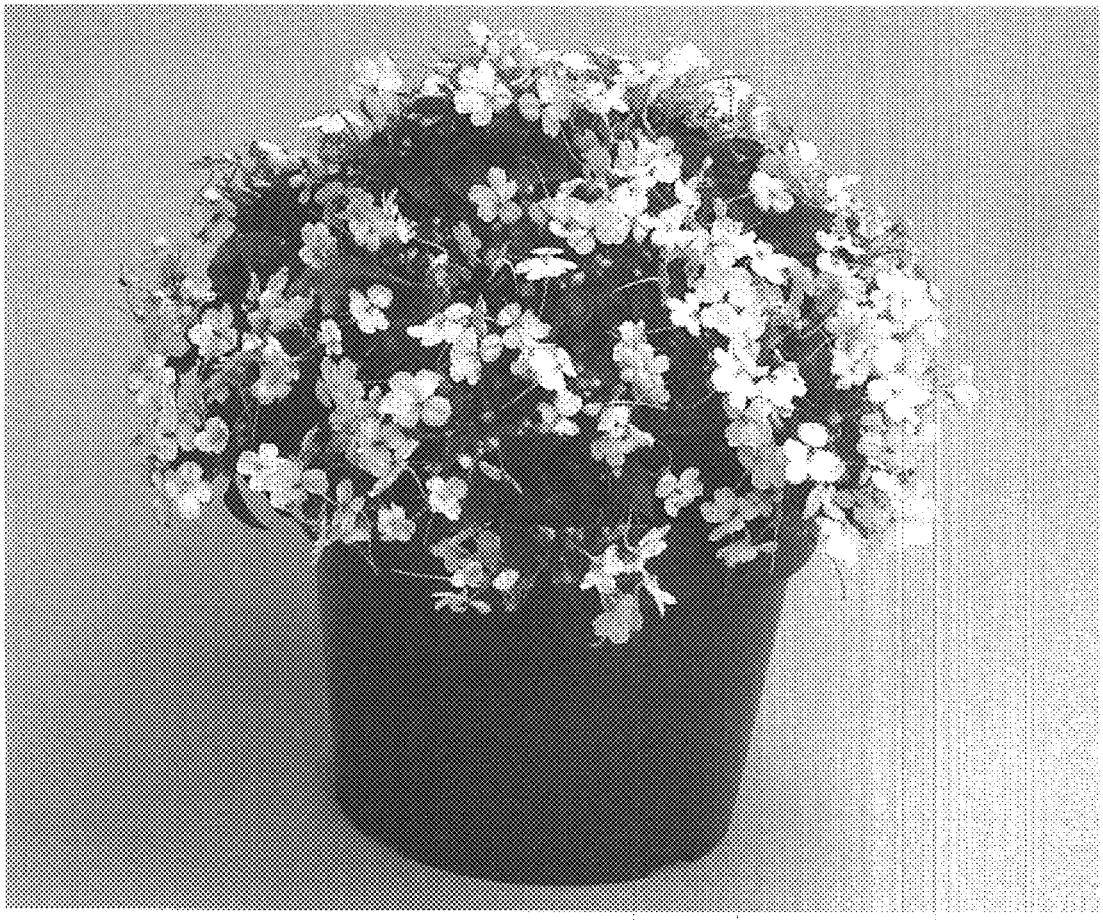
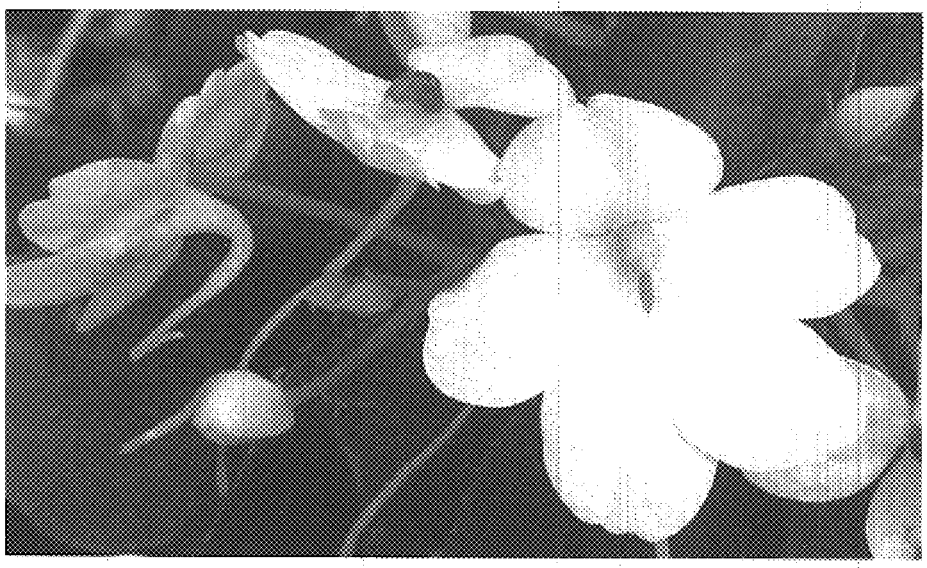

* * * * *